(12) United States Patent
Coop

(10) Patent No.: US 7,637,958 B2
(45) Date of Patent: Dec. 29, 2009

(54) PROSTHETIC LOCKING DEVICE

(75) Inventor: Brian T. Coop, Soddy Daisy, TN (US)

(73) Assignee: Fillauer, Inc., Chattanooga, TN (US)

( * ) Notice: Subject to any disclaimer, the term of this patent is extended or adjusted under 35 U.S.C. 154(b) by 147 days.

(21) Appl. No.: 11/039,427

(22) Filed: Jan. 18, 2005

(65) Prior Publication Data
US 2005/0131550 A1 Jun. 16, 2005

Related U.S. Application Data

(63) Continuation of application No. 10/121,196, filed on Apr. 12, 2002, now abandoned.

(51) Int. Cl.
A61F 2/80 (2006.01)
(52) U.S. Cl. ........................................................ 623/36
(58) Field of Classification Search ............... 623/32–38
See application file for complete search history.

(56) References Cited

U.S. PATENT DOCUMENTS 6,402,789 B1 * 6/2002 Gramnas ..................... 623/38

6,440,173 B1 * 8/2002 Meyer ......................... 623/36

FOREIGN PATENT DOCUMENTS

SE 518263 9/2002

* cited by examiner

Primary Examiner—Alvin J Stewart
(74) Attorney, Agent, or Firm—Miller & Martin PLLC

(57) ABSTRACT

A device is provided to lock the residual limb of an amputee into a prosthesis. The device is comprised of rolling elements within a tapered housing which accepts a smooth plunger, such as a wire, cable, or rod connected to a suspension sleeve, with minimal resistance while opposing removal of the plunger from the locking device until the rolling elements have been retracted with a release mechanism. The nature of this device allows it to compensate for irregularities or wear in the plunger while continuing to securely lock the prosthesis to the sleeve. This locking device will function properly with a certain amount of misalignment between the lock and the plunger.

3 Claims, 6 Drawing Sheets

PROSTHETIC LOCKING DEVICE

RELATED APPLICATIONS

The present application is a continuation of U.S. Ser. No. 10/121,196 filed Apr. 12, 2002 which is being allowed to become abandoned.

FIELD OF THE INVENTION

The present invention is an improved locking device for attaching a prosthesis to a suspension sleeve on a residual limb.

BACKGROUND OF THE INVENTION

Various methods of attaching a prosthesis to an amputee's residual limb have been utilized over the years. Despite advances in materials and design many of the older methods are still being used. The earliest methods were strap and belt type suspension systems. In this design, the amputee inserted the residual limb into the prosthesis and tightened a belt, typically made from leather, to hold the prosthesis to the limb. This design was fraught with practical difficulties, but for many years was the only design available. A second-generation design improvement uses flexible inner integral suction suspension sockets. These designs are especially useful for above-knee prostheses. The amputee simply pulls the prosthesis over the residual limb, while the flexible interior of the socket adheres to the limb creating a vacuum that suctions the prosthetic in place. A valve is installed within the socket to break the suction.

More recent designs have employed mechanical connectors, combined with a removable roll-on suction suspension sleeve. These mechanical connectors consist of: 1) lanyard systems utilizing a braided or twisted polymeric cord attached to the end of the suction suspension sleeve which passes through the socket where it can be secured external to the prosthesis; 2) shuttle lock systems, having a ring attached to the suspension sleeve to receive a pin inserted through the socket; 3) a ratchet type shuttle lock system, using a barbed plunger extending from the end of the suction suspension sleeve and engaging a ratchet mechanism on the prosthesis; and 4) gear driven clutch lock systems using a plunger with teeth to engage a gear mounted to a shaft turning on a one-way bearing where the plunger once engaged with the gear is restricted from upward vertical movement.

Most recently, smooth pin lock systems have been devised in an attempt to overcome the drawbacks of the earlier mechanical lock systems such as Gramnas U.S. Pat. No. 5,298,290 ('290). Gramnas uses a washer to lock the plunger. The washer is housed such that when the plunger pierces the interior of the washer the washer becomes biased against the plunger by springs, which flank the washer. The springs are actuated by a single bearing. The bearing serves to compress one spring while leaving the other to bias the washer against the interior of the housing. Thus the washer becomes angled and the plunger is prevented from exiting the lock. Because the Gramnas design does not rely on gears or ratchets to secure the sleeve to the socket less play is introduced into the lock. Despite the improvements that the smooth pin lock system offers, it has not been a complete solution and has introduced its own disadvantages.

All of the automatic locking mechanical connectors (ratcheting shuttle, gear driven clutch, and smooth pin) have the drawback of requiring the plunger and the lock to be aligned on the same axis. The nature of the design of the ratcheting shuttle and gear driven clutch type locks permits a certain amount of play or backlash that allows the residual limb to piston within the socket. The lanyard and shuttle lock systems do not automatically lock and cannot accommodate volume changes in the residual limb without manual adjustments. Volume changes occur as the amputee bears weight on the residual limb causing swelling or shrinkage in the fleshy portion of the residual limb. Limb shrinkage loosens the fit in the socket and causes the residual limb to slip deeper into the prosthesis. The practical result is that additional play is introduced requiring the amputee to make frequent adjustments to maintain a snug fitting. The ratcheting shuttle lock also suffers from this drawback because the discrete locking steps are spaced too widely to make fine adjustments.

Smooth pin systems must conform to tight tolerances in order to work properly. As components wear, the retention of the prosthesis becomes less secure. This is particularly true in smooth pin systems such as the Gramnas invention, where the smooth pin is restricted from moving out of the lock by a washer that contacts the plunger with a narrow and limited surface area. Over time, the limited surface area of the washer becomes worn, introducing unwanted play or backlash into the locking mechanism. An additional drawback to the washer design is that it is incapable of accepting flexible plungers because the angle generated by the washer is insufficient to prevent a flexible plunger from snaking out of the lock housing. The design therefore requires the plunger and the lock to be aligned on the same axis. When the lock is manufactured with less than perfect alignment in the socket the washer is subject to extraordinary wear causing the locking mechanism to fail prematurely.

A further drawback common to all the mechanical connectors is that they are necessarily manufactured with materials that can withstand the rigors of the locking mechanism. Commonly, the moving and contacting parts are fabricated from high carbon bearing grade steel and hardening the various parts, such as by heat treatment. Such steel bearing grade parts, however, are highly subject to corrosion, particularly when the prosthesis is used in environments offering exposure to liquids or other contaminants. Internal corrosion of the locking device can lead to seizure and failure of the moveable components.

Efforts to overcome the corrosion problem by forming the moving components of a corrosion resistant metal alloy, such as austenitic stainless steel (type 300 series) typically are not practical since such corrosion resistant steel cannot be hardened to the extent necessary for satisfactory life of the moving components. Alternately, forming the moving components of martensitic stainless steels, such as 440C, may provide a bearing grade steel which is hardenable. However, the corrosion resistance is less than that of the 300 series stainless steels. The result is that neither grade of stainless is suitable for the current lock designs. Therefore, amputees that live active lifestyles, who are prone to get their prosthesis wet are forced to live with locking mechanisms that corrode or fail to operate with peak efficiency.

The present invention addresses these potentially troublesome issues while combining the ease of use of an automatic lock with the stepless adjustability of the clutch and smooth pin lock.

BRIEF SUMMARY OF THE INVENTION

This invention is designed to securely lock a sleeve fitted to the amputee's residual limb to a corresponding prosthesis without discrete steps and with little to no backlash during engagement. The invention utilizes a plunger on the sleeve, which is engaged in the prosthesis then detaches when a release mechanism is operated. Rolling elements in the prosthesis portion lock onto the plunger without the need to hold it in perfect alignment, allowing a certain amount of angular misalignment when mounting the lock in the prosthesis. Because the lock is permanently molded or laminated into the socket of the prosthesis during fabrication, a design that can function with imperfect alignment offers advantages to the manufacturer or technician by reducing the likelihood that the prosthesis would need to be re-fabricated. Such a design, also offers advantages to the amputee by reducing the difficulty of adapting to a poorly aligned socket.

This device is also designed to compensate for dimensional variances in the plunger that may occur between plungers of different construction, for example, solid wire or flexible stranded cable, as well as variances that may occur throughout the life of the plunger due to wear.

Another significant advantage of the invention, not addressed by the prior art, is that the moving components, which include the plunger and rolling elements, can be made of softer materials, which are more resistant to oxidation in wet or humid environments. Examples of suitable materials include but are not limited to austenitic stainless steel, titanium, and brass. This feature will allow the amputee to use the locking device in aquatic sports with less concern of the lock rusting or corroding.

DETAILED DESCRIPTION OF THE INVENTION

Figure 1:
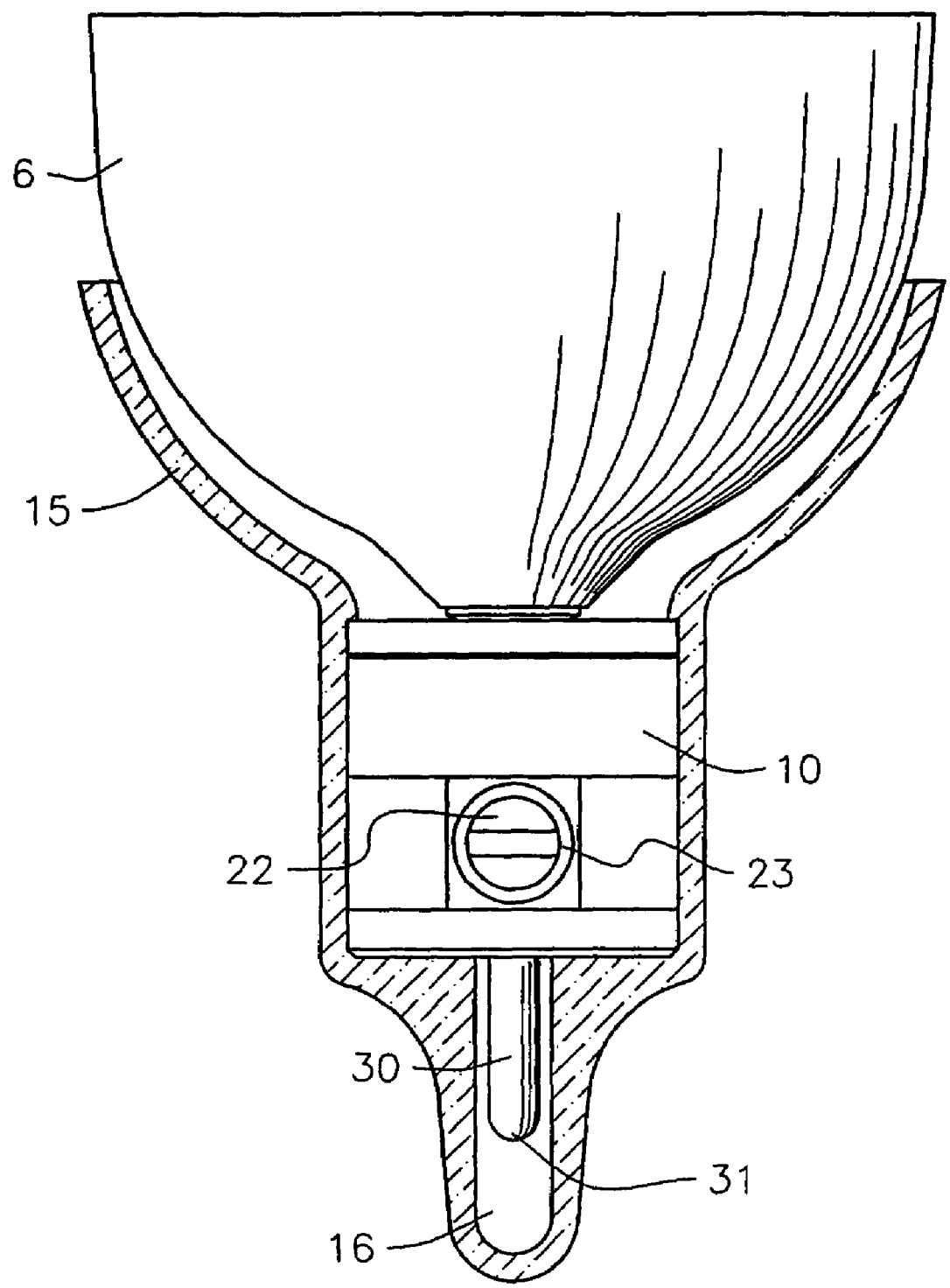
FIG. 1 is a partial sectional view of a prosthetic socket containing a prosthetic lock according to the invention.

Referring now to the drawings and in particular to FIG. 1, a cross-sectional view of a prosthetic socket 15 with a smooth plunger 30 engaged in a locking device 10 is shown. The plunger 30 is attached to the distal end of a sleeve 6 adapted to fit over the residual limb of an amputee. Typical sleeve materials are urethanes, thermoplastic elastomers, or silicone based polymers. The socket 15 and locking device 10 are secured to the proximal end of a prosthesis, typically a prosthetic limb. The plunger 30 is shown fully engaged within the locking device 10. The distal end 31 of the plunger has passed through the locking device 10 and occupies the prosthetic socket plunger cavity 16. The plunger 30 may be tubular or rigid as depicted in FIG. 2a, or flexible such as the braided or twisted cable depicted in FIG. 6.

In a preferred embodiment the plunger 30 should be substantially smooth along its length, however, as in the case of braided cable, ridges in and around the circumference of the plunger 30 are not objectionable. In addition, the plunger 30 should not be limited to a cylindrical form and may also be a multifaceted prismatic member (triangular, rectangular, hexagonal, etc.). Typically, the locking device 10 contains a release mechanism 19 that detaches the plunger 30 by depressing a release button 22, shown in FIG. 1. Also shown is button shield 23 to prevent accidental release of the locking device 10. The release mechanism 19 is not essential to the success of the invention and may be any one of a variety of means to disengage the plunger 30 from the locking device 10. For instance, cam mechanisms that are linearly or radially actuated, a pin hinged linkage, or gear-to-gear or gear-to-rack mechanisms that may be actuated by a pushing member or a drawing member may be used. An exemplerary release mechanism is disclosed in more detail in FIG. 7.

FIGS. 2a-b, 3a-b, 4a-b, and 5a-b depict the plunger 30, at various stages of engagement with the locking device 10. For convenience of illustration plunger 30 is shown in isolation from sleeve 6 (shown in FIG. 1) in which it is secured during use.

Figure 2B:
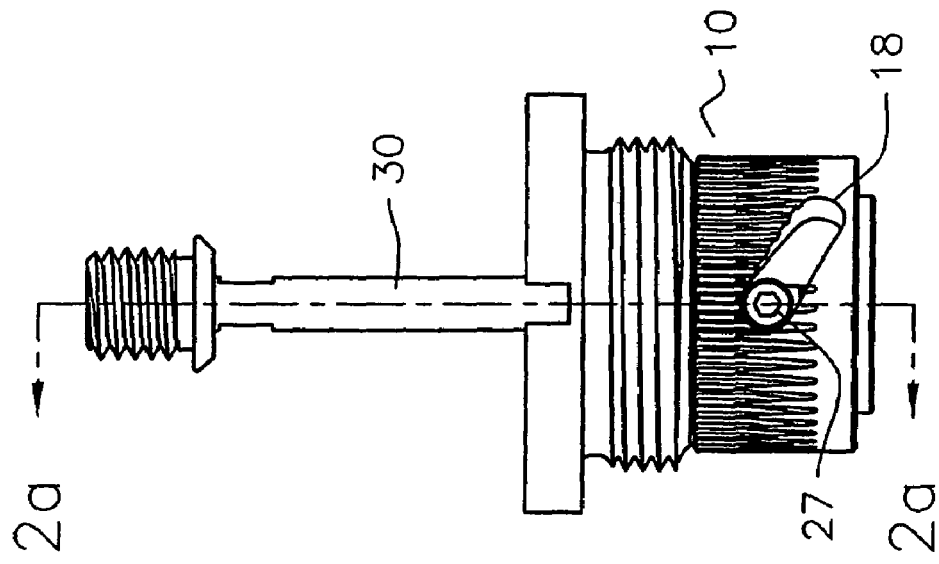
FIG. 2b is a complementary side plan view of the locking device as illustrated in FIG. 2a showing the cam follower at the top of the cam track.
Figure 2A:
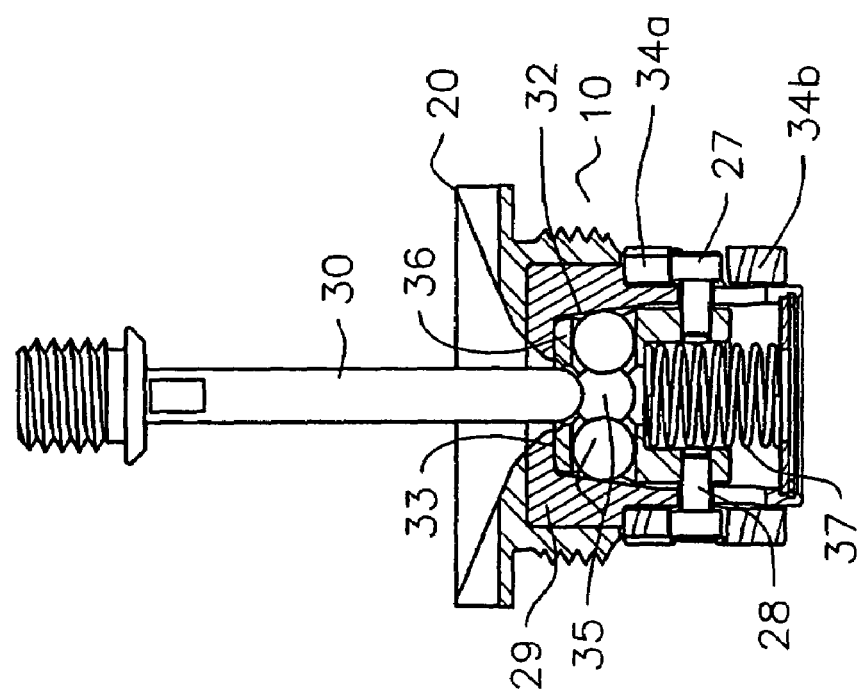
FIG. 2a is a cross-sectional front plan view of a prosthetic lock according to the invention with a plunger in an unlocked position just before making initial contact with a rolling element.

FIG. 2a shows the locking device 10 in an unlocked position with no plunger 30 engaged in the lock. The plunger 30 is shown entering the proximal end of the lock housing 20 just before making initial contact with rolling elements 35. Once separated by the plunger 30, the rolling elements 35 remain in contact with the tapered interior 32 of the clutch lock body 29 due to force applied by a lift such as, lock spring 37, which biases the rolling element retainer 36 to the top most portion 33 of the tapered interior 32. The shape of the rolling elements 35 may be cylindrical, spherical, elliptical or any other shape that allows rolling elements 35 to contact the tapered lock-housing interior 32 when force is applied by the plunger 30. The number of rolling elements 35 may also be variable. The embodiment shown in FIG. 2a has three rolling elements 35 within the rolling element retainer 36, but it is possible to have a larger plurality or only one rolling element 35 in a properly configured retainer 36. For instance, single rolling element 35 requires that at least one interior surface not be tapered. With a single cylindrical rolling element 35, only one wall of the retainer 36 would need to be tapered.

As illustrated in FIG. 2a the rolling elements 35 have not yet begun to be forced outward. Before the plunger comes into contact with the rolling elements 35 the lock spring 37 has not yet been compressed. Cam followers 27 are shown attached by the cam spacers 28 to the rolling element retainer 36. The cam follower 27 are shown between upper cam track wall 34a and lower cam track wall 34b.

FIG. 2b shows the exterior of the locking device 10 and the position of cam follower 27 when plunger 30 is in the uncompressed position depicted in FIG. 2a. The cam follower 27 is at the top of radial cam track 18.

Figure 3B:
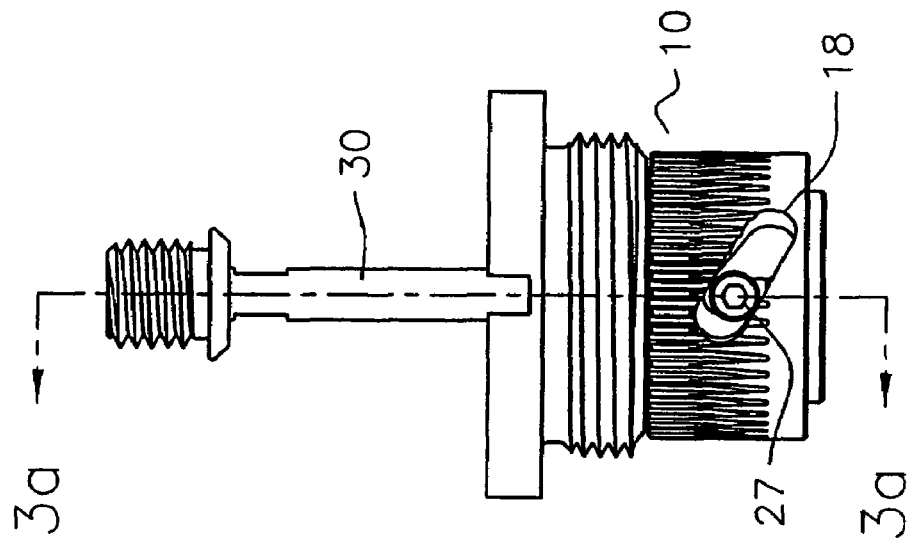
FIG. 3b is a complementary side plan view of the locking device as illustrated in FIG. 3a showing the cam followers descending the cam track in response to the initial compression of the lock spring.
Figure 3A:
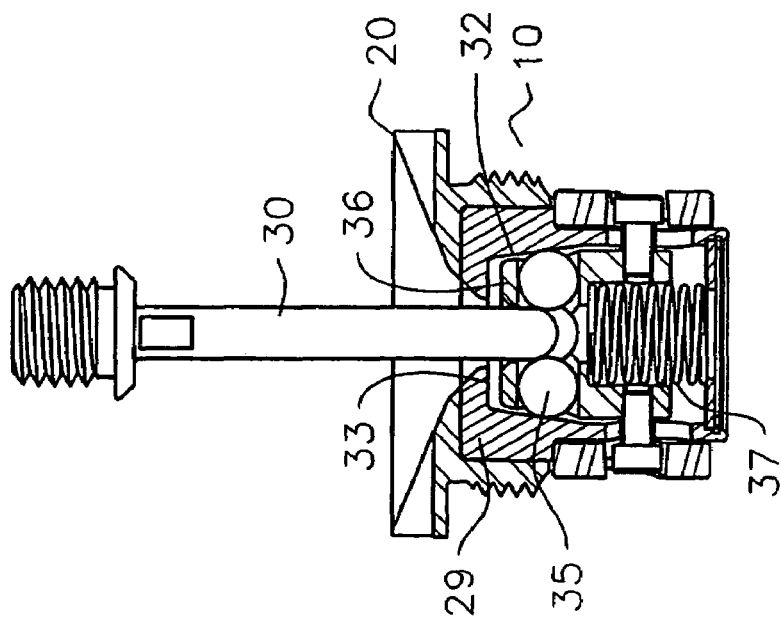
FIG. 3a is a cross-sectional front plan view of a prosthetic lock according to the invention with a plunger contacting a rolling element with sufficient force to compress the lock spring.

FIG. 3a shows the plunger 30 beginning to penetrate the interior of the clutch lock body 29. The downward force placed on the rolling elements 35 begins to compress the lock spring 37. The rolling elements 35 begin to spin or roll along the walls of tapered interior 32 as the plunger 30 is inserted deeper into the clutch lock body 29. The rolling element retainer 36 and rolling elements 35 descend within the tapered interior 32 of the clutch lock body 29. As illustrated, a small clearance space has developed between the retainer 36 and the top most portion 33 of the tapered interior 32.

FIG. 3b shows the exterior of the locking device 10 and the position of cam follower 27 when the plunger 30 is in the position depicted in FIG. 3a. The cam follower 27 has descended down the cam track 18 a distance, which corresponds to the partial compression of the lock spring 37.

Figure 4B:
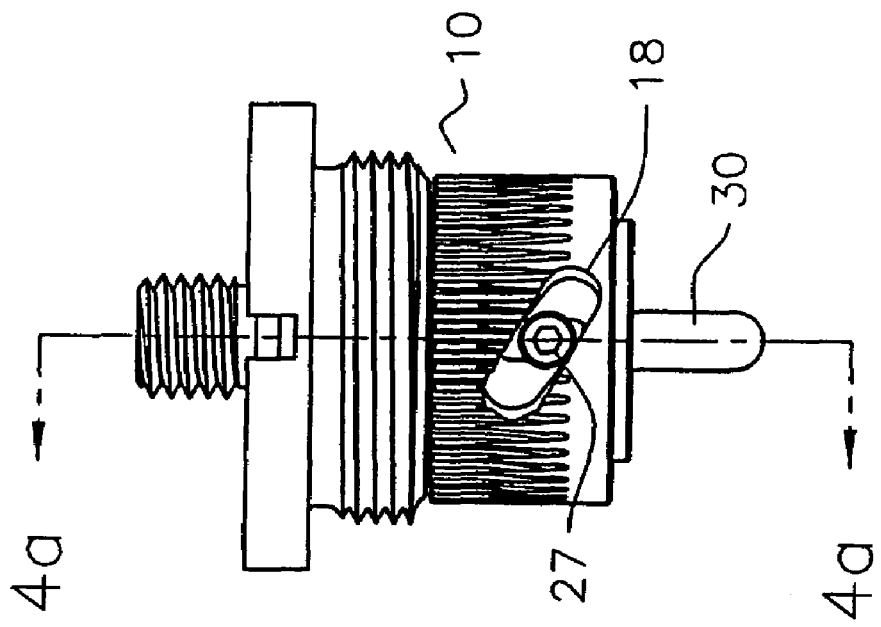
FIG. 4b is a complementary side plan view of the locking device as illustrated in FIG. 4a showing the cam follower descending the cam track in response to the plunger compressing the lock spring to a locking depth.
Figure 4A:
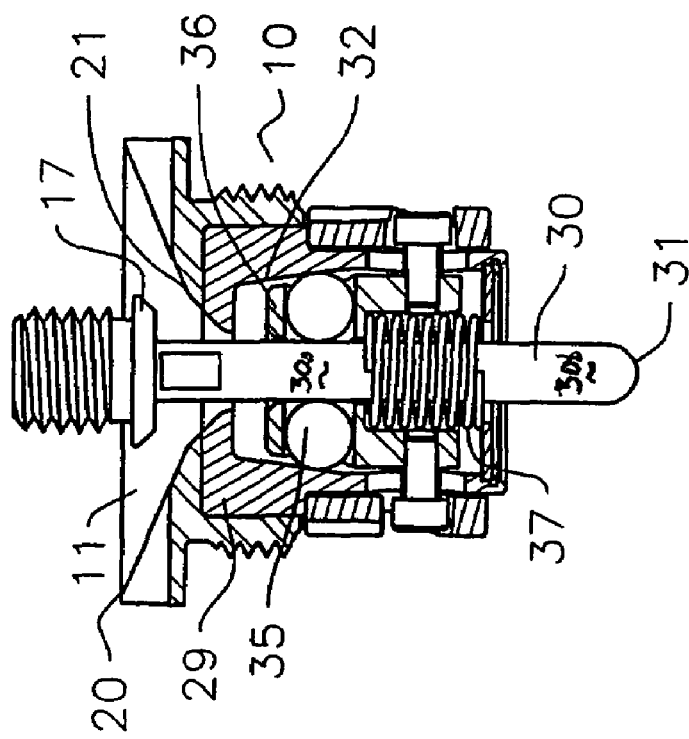
FIG. 4a is a cross-sectional front plan view of a prosthetic lock according to the invention with the plunger in a locked position.

FIG. 4a shows the plunger 30 after fully penetrating the clutch lock body 29. In addition the plunger distal end 31 has passed through the lock spring 37 and out of the locking device 10. Once the distal end 31 has passed the rolling elements 35, and the full diameter of plunger 30 is disposed between those elements 35, the plunger 30 resists removal. Notably, in this locked position the plunger 30 may still pass freely downward through the rolling elements 35 of the locking device 10 until the plunger face 17 strikes the plunger guide 21.

In the locked position shown in FIG. 4a the plunger 30 has moved the rolling elements 35 down the tapered interior 32 to a position where the width of the interior 32 is just adequate to accommodate the plunger 30 and the rolling elements 35. This position generally results after the full diameter of plunger 30 has passed the equator of the rolling elements 35. At this point the plunger 30 cannot be retrieved from the locking device 10 without activating the release mechanism.

After the plunger 30 has passed the equator of the rolling elements 35 it cannot be removed from the locking device 10 because the rolling elements 35 are biased upwards by lock spring 37 and inwards against plunger 30 by the tapered interior 32. Pulling the plunger 30 upward in the direction that would remove it from the lock 10 causes the plunger 30 to frictionally interface with rolling elements 35, which are thereby encouraged to roll up the tapered interior 32 of the clutch lock body 29. This action causes the rolling elements 35 to be even more tightly compressed against the plunger 30. Because rolling elements 35, plunger 30 and the tapered interior 32 are not made of compressible material, the plunger 30 and rolling elements 35 in rolling element retainer 36 effectively form a wedge, which cannot be moved upwards within the lock 10. While the rolling elements 35, plunger 30 and tapered interior 32 are not made of compressible material, they are preferably made of softer more corrosion resistant materials than prior art prosthetic locking devices. Examples include corrosion resistant grades of stainless steel, titanium, and other corrosion resistant alloys. This is possible because the invention, unlike prior locks, displaces wear over a larger surface area and requires less force to initially secure and hold the prosthesis in place. Because the rolling elements 35 roll and spin during the locking process no single portion of the rolling elements 35 consistently contacts the plunger 30. The plunger 30 also being cylindrical offers more surface area to contact the rolling elements. The use of a plurality of spherical rolling elements acts to both distribute the contacting portions of rolling elements 35 over the entire surface of those elements, and to maximize the number of contacts between plunger 30 and rolling elements 35.

FIG. 4b shows the exterior of the locking device 10 and the position of cam follower 27 when plunger 30 and retainer 36 are positioned as depicted in FIG. 4a. The cam follower 27 has descended down the cam track 18 a distance, which corresponds to the partial compression of the lock spring 37. The lock spring 37 does not need to compress further to accommodate any length of plunger 30, because the width of the tapered interior 32 is adequate at this point to accommodate the plunger 30 and the rolling elements 35. Thus even as the plunger 30 is inserted further until the plunger face 17 interfaces with guide 21, there is no additional downward pressure to further compress the lock spring 37.

Figure 5B:
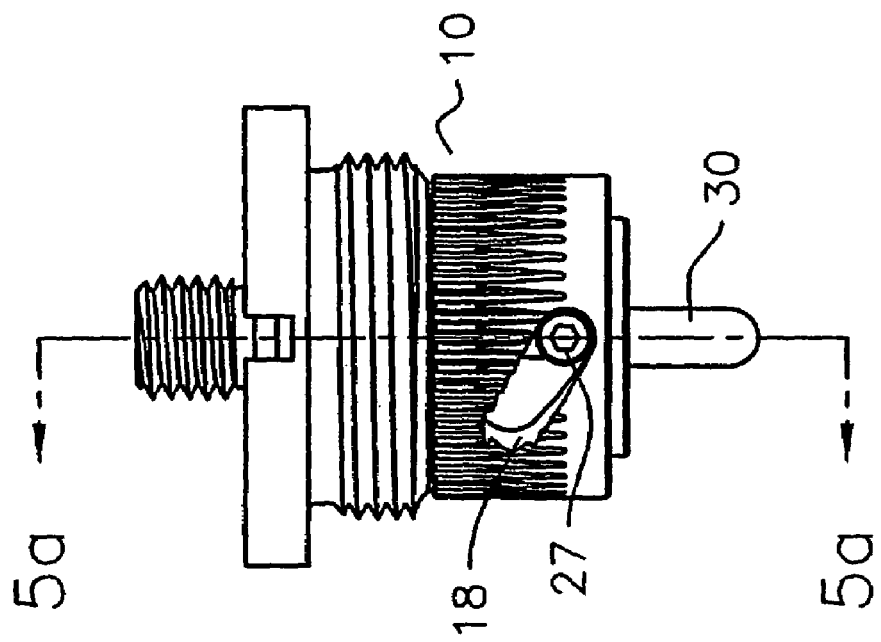
FIG. 5b is a complementary side plan view of the locking device as illustrated in FIG. 5a showing the cam follower fully descended along the cam track to an unlocking position.
Figure 5A:
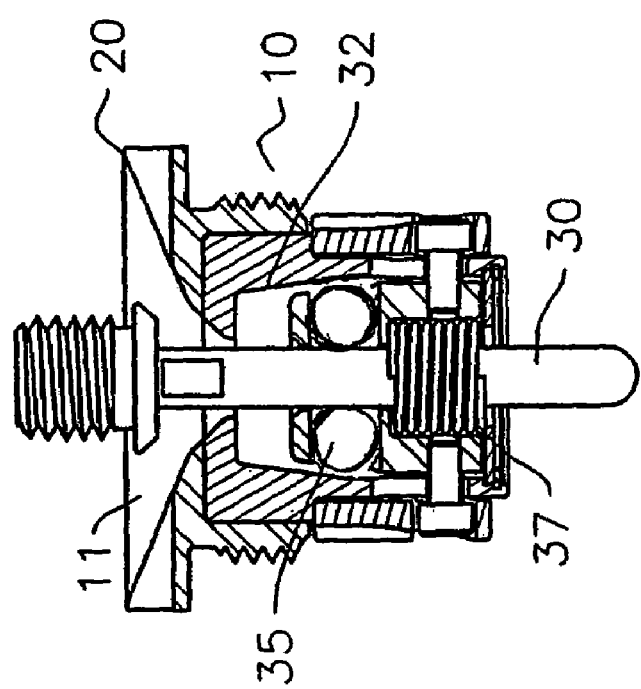
FIG. 5a is a cross-sectional front plan view of the prosthetic lock according to the invention with the plunger released from the locked position by the release mechanism.

FIG. 5a shows the plunger 30 in an unlocked position as the release mechanism has compressed the lock spring 37 to the extent that the rolling elements 35 are no longer in intimate contact with both the plunger 30 and the tapered interior 32. So long as the release mechanism holds the lock spring 37 in this compressed position the plunger 30 can be pulled back through the top 11 of the locking device 10, because the rolling elements 35 will not simultaneously engage both plunger 30 and tapered interior 32 and roll upward as the plunger 30 is removed.

FIG. 5b shows the exterior of the locking device 10 and the position of cam follower 27 when the retainer 36 is in the position depicted in FIG. 5a. The cam follower 27 has descended to the bottom of the cam track 18, a distance, which corresponds to the nearly total compression of the lock spring 37. The cam follower 27 is typically placed in this position by a radially actuated release mechanism. A linearly actuated release mechanism is disclosed in greater detail below in connection with FIG. 7.

Figure 6:
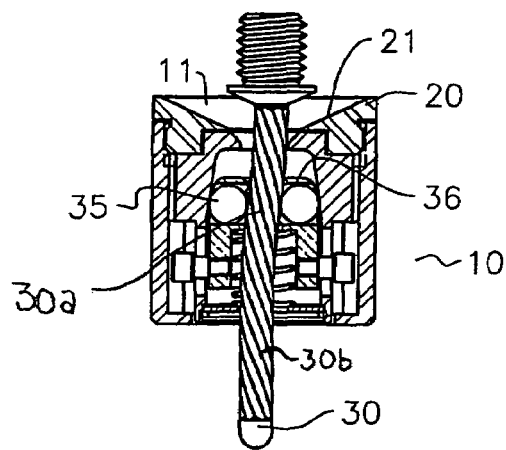
FIG. 6 is a partial section front plan view of a prosthetic lock according to the invention with a flexible plunger with an off-axis translation

FIG. 6 illustrates a unique feature of the present invention, which allows flexible plungers 30 to enter the locking device 10 at irregular angles while maintaining reliable locking function. This is particularly beneficial when the locking mechanism has been cast into the prosthetic socket or limb at an imperfect angle. As shown in FIG. 6 the plunger 30 has entered the locking device 10 at a slight angle from the right side of the plunger guide 21. The rolling elements 35 accommodate the angled entry directing the plunger 30 through the rolling element retainer 36 and the locking device 10 while establishing a reliable lock. As previously described once the full diameter of plunger 30 has passed the equator of the rolling elements 35 it cannot be removed through the locking device top 11. Other locking devices that allow angular plunger 30 entry usually impart some amount of play in the locking hold. The present invention provides a consistent lock while minimizing any play or looseness due to an angled entry. Furthermore, it should be noted that both the shank portion 30a that is gripped by the lock and the stem portion 30b that leads the plunger 30 into the locking device are flexible.

Figure 7:
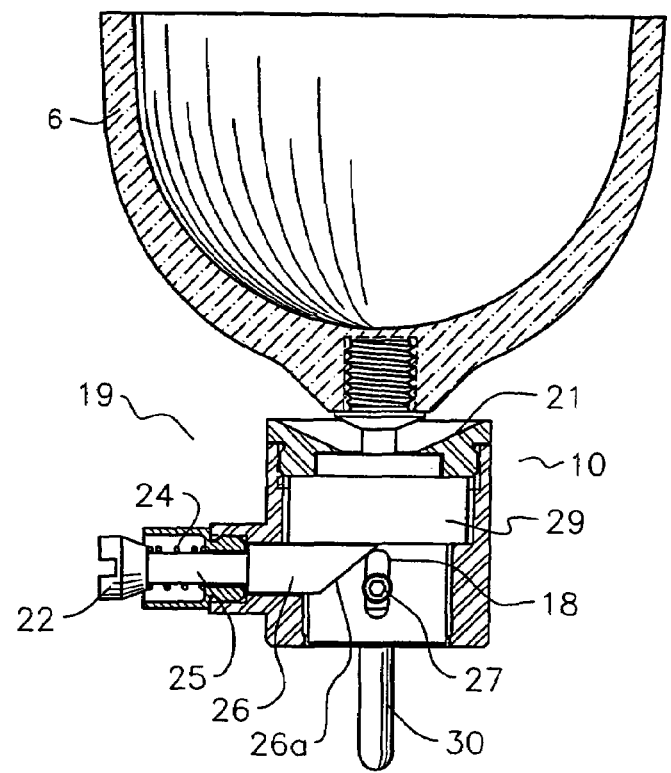
FIG. 7 is a partial section view of a prosthetic release mechanism according to the invention.

FIG. 7 illustrates one embodiment of the release mechanism 19 that can be used with the invention. The plunger 30 is shown fully engaged within the locking device 10. The plunger 30 is released by pressing the release button 22 that communicates via release pin 25 to release cam 26. The release cam 26 has a downwardly slanted face 26a, which pushes the cam follower 27 downward in the linear cam track 18 in the clutch lock body 29. Cam follower 27 is connected to the rolling element retainer 36. As the downward slanted face 26a passes over cam followers 27, both cam followers 27 and attached rolling element 36 move downward compressing the lock spring 37 to the extent shown in FIG. 5. The rolling element retainer 36 also moves the rolling elements 35 downward within the tapered interior 32 to a wider portion. The width of the tapered interior 32 at this point is such that rolling elements 35 do not simultaneously contact both the plunger 30 and the tapered interior 32 of the clutch lock body 29, thereby effecting the release of the plunger 30 from the locking device 10. Release button 22 is normally held in the locked position by the release spring 24 and may be protected from accidental actuation by a button shield 23 as shown in FIG. 1.

While a preferred embodiment has been shown and described, it will be understood that it is not intended to limit the disclosure, but rather it is intended to cover all modifications and alternate methods falling within the spirit and the scope of the invention as defined in the appended claims.

What is claimed is:

1. A method of detaching a prosthetic sleeve having a longitudinally smooth plunger passing through the opening to the top interior portion of a lock housing and engaged in the locking device, the locking device and comprising a lock housing having an exterior, a tapered interior, with a top interior portion, and an opening passing through the top interior portion to the exterior; a substantially smooth rolling element housed within said tapered interior; a spring biasing said rolling element towards the top portion of the tapered interior; and a release mechanism which moves the rolling element away from the top portion of the tapered interior when activated;

Said method comprising the steps of:
   (a) activating the release mechanism to move the rolling element distally away from the top opening;
   (b) continuing distal movement of the rolling element until the width of the tapered interior is sufficient that the rolling element does not simultaneously contact both the tapered interior and the longitudinally smooth plunger; and
   (c) withdrawing the plunger out through the top opening.

2. The method of claim 1, wherein the release mechanism is actuated by pulling a draw member connected to the release mechanism.

3. The method of claim 2, wherein the plunger is in a form selected from the group consisting of solid wire, rod, and stranded flexible wire.

* * * * *